Figure 4:
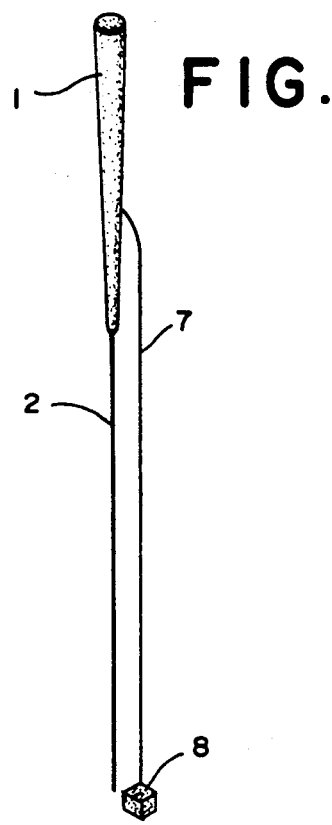

United States Patent [19]
Hwang

[11] Patent Number: 5,089,001
[45] Date of Patent: Feb. 18, 1992

[54] INJECTION MOLDING ACUPUNCTURE ACUS WITH DOUBLE SAFETY DEVICE

[76] Inventor: C. H. Hwang, 14, Nung 6, Lane 315, Chung-shan N. Rd., San-chung City, Taiwan

[21] Appl. No.: 433,236

[22] Filed: Nov. 8, 1989

[51] Int. Cl.$^5$ .............................................. A61B 17/34
[52] U.S. Cl. ...................................... 606/189
[58] Field of Search .............. 606/189, 181; 206/365, 206/370; 604/192, 198, 263; 128/907

[56] References Cited

U.S. PATENT DOCUMENTS

| | | | |
|---|---|---|---|
| 3,134,380 | 5/1964 | Armao | 604/198 |
| 3,905,375 | 9/1975 | Toyama | 606/189 |
| 4,479,496 | 10/1984 | Hsu | 606/189 |
| 4,564,054 | 1/1986 | Gustavsson | 604/198 |
| 4,580,566 | 4/1986 | Hsu | 606/189 |
| 4,725,267 | 2/1988 | Vaillancourt | 604/192 |
| 4,915,697 | 4/1990 | DuPont | 604/192 |

FOREIGN PATENT DOCUMENTS

| | | | |
|---|---|---|---|
| 3522855 | 3/1986 | Fed. Rep. of Germany | 606/189 |
| 2600530 | 12/1987 | France | 606/189 |

OTHER PUBLICATIONS

Abstract of U.S. Pat. No. 4,832,696, Assembly of Needle and Protector, Ronald Luther and Pradip V. Choksi.
Abstract of U.S. Pat. No. 4,850,374, Blood Sampler with Retractable Needle, Nydia Diaz-Ramos and Rio Pierdras.

Primary Examiner—C. Fred Rosenbaum
Assistant Examiner—William W. Lewis
Attorney, Agent, or Firm—Bacon & Thomas

[57] ABSTRACT

The present invention is related to an improved structure of an acupuncture acus, especially a multiple safety acupuncture acus provided with a bellow protector. The grip of the said acupuncture acus is produced by injection molding and is in the form of a cone flange which can be engaged exactly by a protective sleeve for convenience of packing; a bellow type protector is built from the adjoining position between the acupuncture acus and the grip to the needle head; the end of the protector is in the form of a hollow ring, its inside ring is made of membrane, while its outer ring is made of soft plastic. In application, the peripheral surface shaped by the hollow ring can be used by the beginner as a buffer prior to needle piercing and make corresponding adjustment, while the acupuncture acus is pierced through the membrane of the inside ring and into the right part of patient, the bellow will be compressed immediately and become tightened, and after the acupuncture acus is pulled out, the bellow will return to its original state and wrap the acupuncture acus to form another safety measure; the outer hollow ring sheath is made of soft plastic, so that the acupuncture acus, after application can be inserted at the inside of the outer ring to form yet another safety measure.

2 Claims, 2 Drawing Sheets

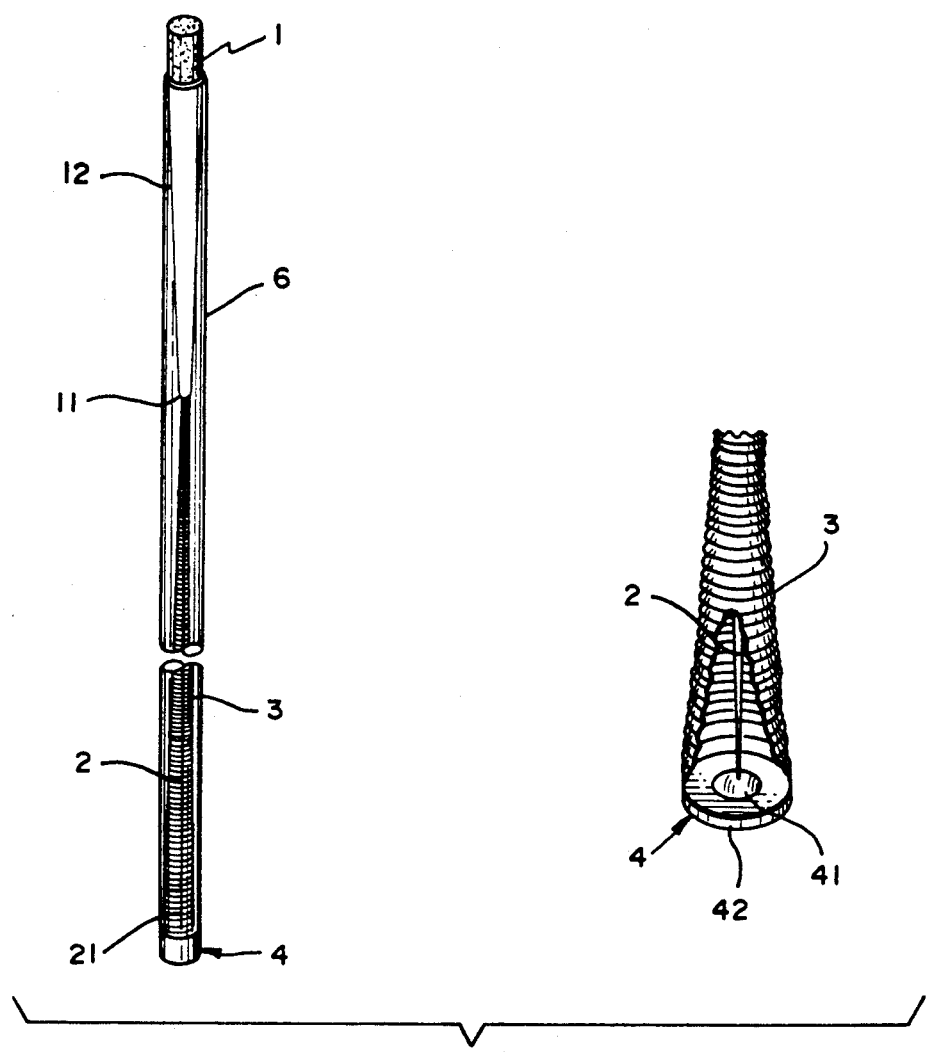
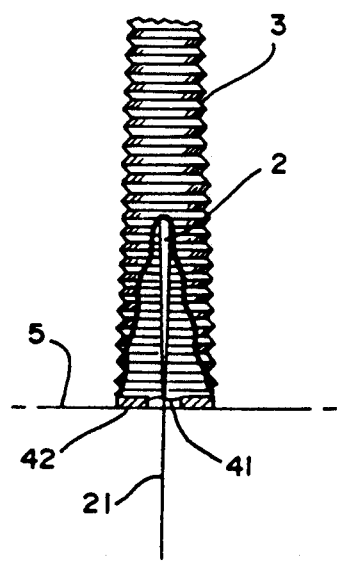
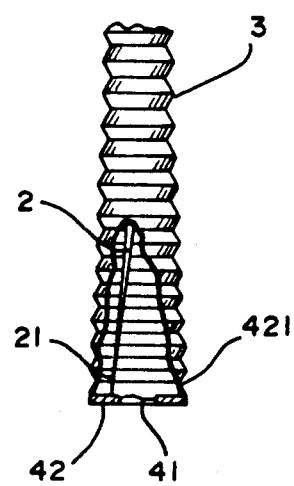
FIG. 1
FIG. 2
FIG. 3

INJECTION MOLDING ACUPUNCTURE ACUS WITH DOUBLE SAFETY DEVICE

BACKGROUND OF THE INVENTION

The present invention is related to an acupuncture acus provided with a bellow protector. The grip of the said acupuncture acus is produced by injection molding and at the same time the said bellow protector serves as the packing external protector for the acupuncture acus, wherein a cone flange of the grip of acupuncture acus can be engaged exactly by a protective sleeve to achieve a double safety measure. A bellow type protector is built from the adjoining position between the acupuncture acus and the grip to the needle head in form of a hollow ring defined by an internal ring formed of membrane, and an outer ring formed of soft plastic. In application, the peripheral surface shaped by the hollow ring can be used by the user as a buffer prior to needle piercing and make corresponding adjustment, while the acupuncture acus is pierced through the membrane of the internal ring and into the patient, during which the bellow will be compressed immediately and tightened, and after the acupuncture acus is pulled out, the bellow will return to its original state and wrap the acupuncture acus, thereby forming another safety measure.

Figure 7:
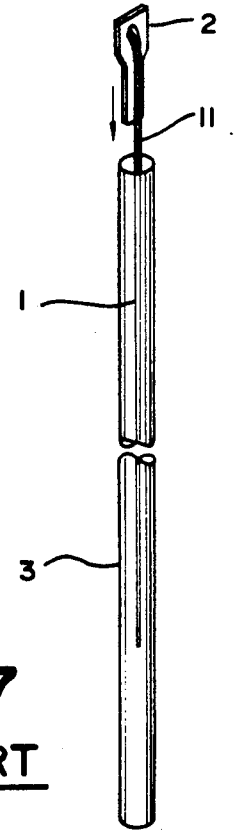

It is well known that the conventional acupuncture acus available on the market has its grip coiled by metal wires or extruded by aluminum material, and packed by using a wafer (2) to catch the grip (11) and fixed at the inside wall of a pipe (3), as seen in FIG. 7. A structure and packing of such kind of acupuncture acus has the following disadvantages: (1) due to high production cost, it is very expensive, and consumers often use them for the second time after sterilization, in case of insufficient sterilization, it might be cause post trouble;(2) the packing is unsafe, if the wafer accidentally falls off, the acupuncture acus will be dropped immediately and hurt somebody. Morever, the used acupuncture has no safety protection measure during disposal procedure and might cause serious medical pollution.

In view of the said problem, a structure of acupuncture acus of the present invention is thus created to provide the multiple safety protection functions.

SUMMARY OF THE INVENTION

The main object of the present invention is to provide an injection molded acupuncture acus produced by series-production to reduce the production cost, in order to avoid the disadvantages caused by its second time application. Another object of the present invention is to provide multiple safety protection functions of its structure, in order to prevent any injury to medical people or a third party after application of the acupuncture acus so as to avoid unnecessary medical pollution.

The above-described and other objects, features and advantages of the present invention will be more apparent from the following description taken in conjunction with the drawings, wherein:

FIG. 1: a schematic drawing of a first preferred embodiment of the present invention;

FIG. 2: a schematic drawing of the present invention under application;

FIG. 3: a schematic drawing of the present invention after application.

FIG. 4 a schematic drawing of a second preferred embodiment of the present invention.

Figure 5:
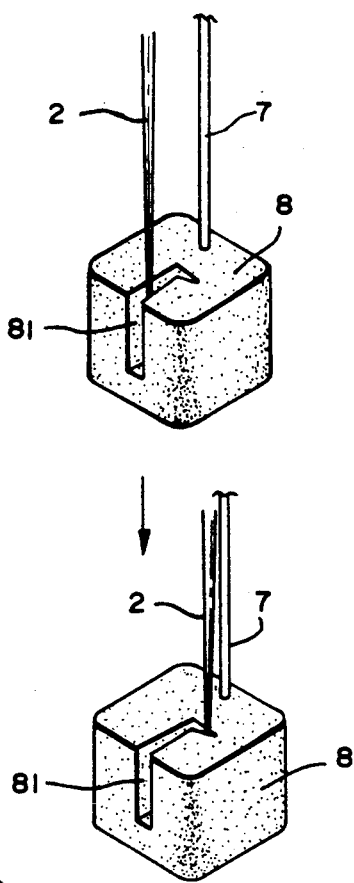
Figure 6:
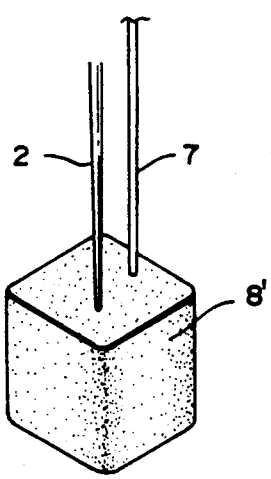

FIG. 5: a schematic drawing showing the acupuncture acus engaged on a soft plastic block;

FIG. 6: a schematic drawing showing the acupuncture acus inserted directly on a soft plastic block;

FIG. 7: a schematic drawing of a conventional acupuncture acus and its packing method.

Referring to FIG. 1, there is shown a schematic drawing of a first preferred embodiment of the present invention. One can clearly see that from the adjoining position (11) between the grip (1) of the acupuncture acus and the acus part (2) to the acus head (21) is arranged with a bellow protector (3) and in fact the end of the said protector (3) comprises a hollow ring (4), whereby ring (4) includes an internal ring (41) in the form of a membrane, and an external ring (42) integrally injected out of soft plastic. When the user uses it, he should hold its grip (1) the latter having various kinds of friction surface threads required for gripping. This facilitates needle twisting and/or needle piercing, especially the hollow ring body (4) of the bellow protector permits a beginner to adjust position so that he can pierce with more accuracy into the correct position of the patient, and while the user is piercing the acupuncture acus into the patients's skin (5) (Please refer to FIG. 2), the bellow (3) will be tightened against the skin of the patient, and after the acus is pulled out of the skin, it will then be returned to the original state as shown in FIG. 1 and enclosed with a layer of protection, so as to avoid the hazard of the used acus injuring somebody. An essential feature of the invention resides in the bellow protector (3) being provided with the hollow ring (4) having the external ring made of soft plastic so that one can insert the used acupuncture acus directly into an inside wall (421) of the external ring (42) and secure the second protection measure, as shown in FIG. 3.

FIG. 1 is a schematic drawing of a real object of the present invention, further to the above-described double protection measures, the grip (1) of the said acupuncture acus is provided with a cone flange (12) which is received directly in the inside pipe wall of the external protector (6) and builds a second safety measure, irrespective of prior or subsequent application. The acupuncture, acus according to the invention is perfectly safe and provides no hazard risk at all.

Referring to FIG. 4, thereis shown another preferred embodiment, including a hand grip (1) of the said acupuncture acus, a plastic fine thread (7) and soft a plastic block (8) are injection molded as an integrated part. Before and after application, the acupuncture acus (2) may be engaged and/or inserted on a soft plastic block so as to prevent the acupuncture acus (2) from injuring person.

Referring to FIG. 5, there is shown a schematic drawing of the manner of catching the acupuncture acus (2) on a soft plastic block (8), whereby the motion direction of the said acupuncture acus (2) is moved forward in the direction indicated by the arrow into a concave slot (81) and finally the acupuncture acus (2) is fixed at the bottom of the concave slot (81) of the soft plastic block and thus safety against injury is assured.

Referring to FIG. 6, a schematic drawing showing the acupuncture acus (2) directly inserted and fixed on a soft plastic block (8'). Because the soft plastic block is very soft, the acupuncture acus can be easily inserted into it, so that the acupuncture acus will not injure any person.

In general, as described above, the present invention is to provide a perfect reasonable design, irrespective of the bellow type protector or the hollow ring of the said protector, even the cone flange of the grip of the said acupuncture acus, all can develop respective functions and will meet the requirement of patent claims of improvement and will be a valuable invention.

I claim:

1. An acupuncture acus device having multiple safety protection features, comprising:

a) an acupuncture acus having an acus head;

b) a grip having a cone flange, the grip being operatively connected to the acupuncture acus;

c) protective means engageable by the acus head when the acus head is not being used for acupuncture treatment, the protective means including a soft plastic block means such that the acus head is insertable into the soft plastic block means; and d) means connecting the cone flange with the protective means, the connecting means including a fine thread formed from plastic.

2. The device of claim 1 wherein the grip, fine plastic thread and soft plastic block means are all formed by injection molding.

* * * * *